(12) United States Patent
Sakamoto et al.

(10) Patent No.: US 7,405,316 B2
(45) Date of Patent: Jul. 29, 2008

(54) ORGANOSILICON COMPOUNDS

(75) Inventors: Takafumi Sakamoto, Annaka (JP); Akitsugu Fujiwara, Annaka (JP); Noriko Kameda, Annaka (JP); Tsuneo Kimura, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 11/938,392

(22) Filed: Nov. 12, 2007

(65) Prior Publication Data

US 2008/0114182 A1      May 15, 2008

(30) Foreign Application Priority Data

Nov. 13, 2006     (JP)     ............... 2006-306596

(51) Int. Cl.
*C07F 7/00*    (2006.01)
(52) U.S. Cl. .................................... 556/434
(58) Field of Classification Search ............. 556/434
See application file for complete search history.

(56) References Cited

U.S. PATENT DOCUMENTS 5,272,243 A * 12/1993 Nakashima et al. ........... 528/31
5,948,854 A *  9/1999 de Buyl et al. ............... 524/788

* cited by examiner

*Primary Examiner*—Samuel A Barts
(74) *Attorney, Agent, or Firm*—Westerman, Hattori, Daniels & Adrian, LLP.

(57) ABSTRACT

Silyl ketene acetal compounds having a partial structure of formula (1) wherein R and $R^2$ each are a monovalent $C_1$-$C_{12}$ hydrocarbon group and n is an integer of 1-6 are useful as a terminal alkoxysilylating agent, surface treating agent, storage stabilizer, curing agent or the like

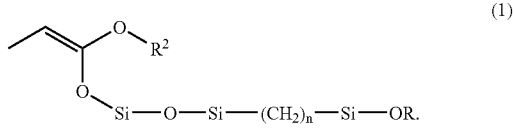

(1)

2 Claims, 20 Drawing Sheets

ORGANOSILICON COMPOUNDS

CROSS-REFERENCE TO RELATED APPLICATION

This non-provisional application claims priority under 35 U.S.C. §119(a) on Patent Application No. 2006-306596 filed in Japan on Nov. 13, 2006, the entire contents of which are hereby incorporated by reference.

TECHNICAL FIELD

This invention relates to novel organosilicon compounds, and more particularly, to novel organosilicon compounds useful as an alkoxysilylating agent, surface treating agent, curing agent, and storage stabilizer or alcohol scavenger.

BACKGROUND ART

A variety of alkoxysilanes are known as the terminal alkoxysilylating agent for organopolysiloxanes such as α,ω-dihydroxypolydimethylsiloxane. For example, tetramethoxysilane, methyltrimethoxysilane, tetraethoxysilane, and other silanes are known. More active silylating agents are disclosed in Japanese Patent No. 2,507,251.

Well-known alkoxysilylating agents, however, are still unsatisfactory in reactivity and other properties. There is a need for alkoxysilylating agents with higher reactivity and other properties.

DISCLOSURE OF THE INVENTION

An object of the invention is to provide novel organosilicon compounds useful as terminal alkoxysilylating agents for organopolysiloxanes.

It has been found that the object is attained by the compounds obtained through hydrosilylation reaction between an acrylic ester or acrylate and a hydroalkoxysiloxane compound, especially by silyl ketene acetal compounds having the formula (2), shown below.

The invention provides a silyl ketene acetal compound having a partial structure of the formula (1);

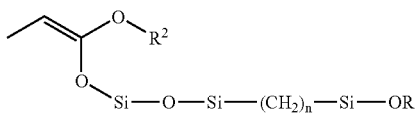

(1)

wherein R and $R^2$ are each independently a substituted or unsubstituted, monovalent hydrocarbon group of 1 to 12 carbon atoms, and n is an integer of 1 to 6.

The typical silyl ketene acetal compounds have the formula (2):

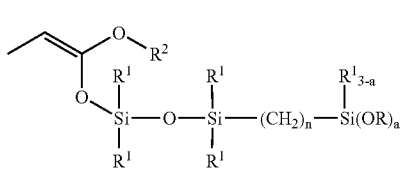

(2)

wherein R, $R^1$ and $R^2$ are each independently a substituted or unsubstituted, monovalent hydrocarbon group of 1 to 12 carbon atoms, n is an integer of 1 to 6, and "a" is an integer of 1 to 3.

BENEFITS OF THE INVENTION

The novel organosilicon compounds of the invention are efficiently reactive with alcohols and silanols, and useful as a terminal alkoxysilylating agent for organopolysiloxanes such as α,ω-dihydroxypolydimethylsiloxane, a surface treating agent for silica, and a scavenger for alcohols, that is, storage stabilizer in alcohol removal type RTV compositions. Also, trifunctional alkoxysilanes having three methoxy groups per molecule are useful as a curing agent in alcohol removal type RTV compositions.

DESCRIPTION OF THE PREFERRED EMBODIMENT

Figure 1:
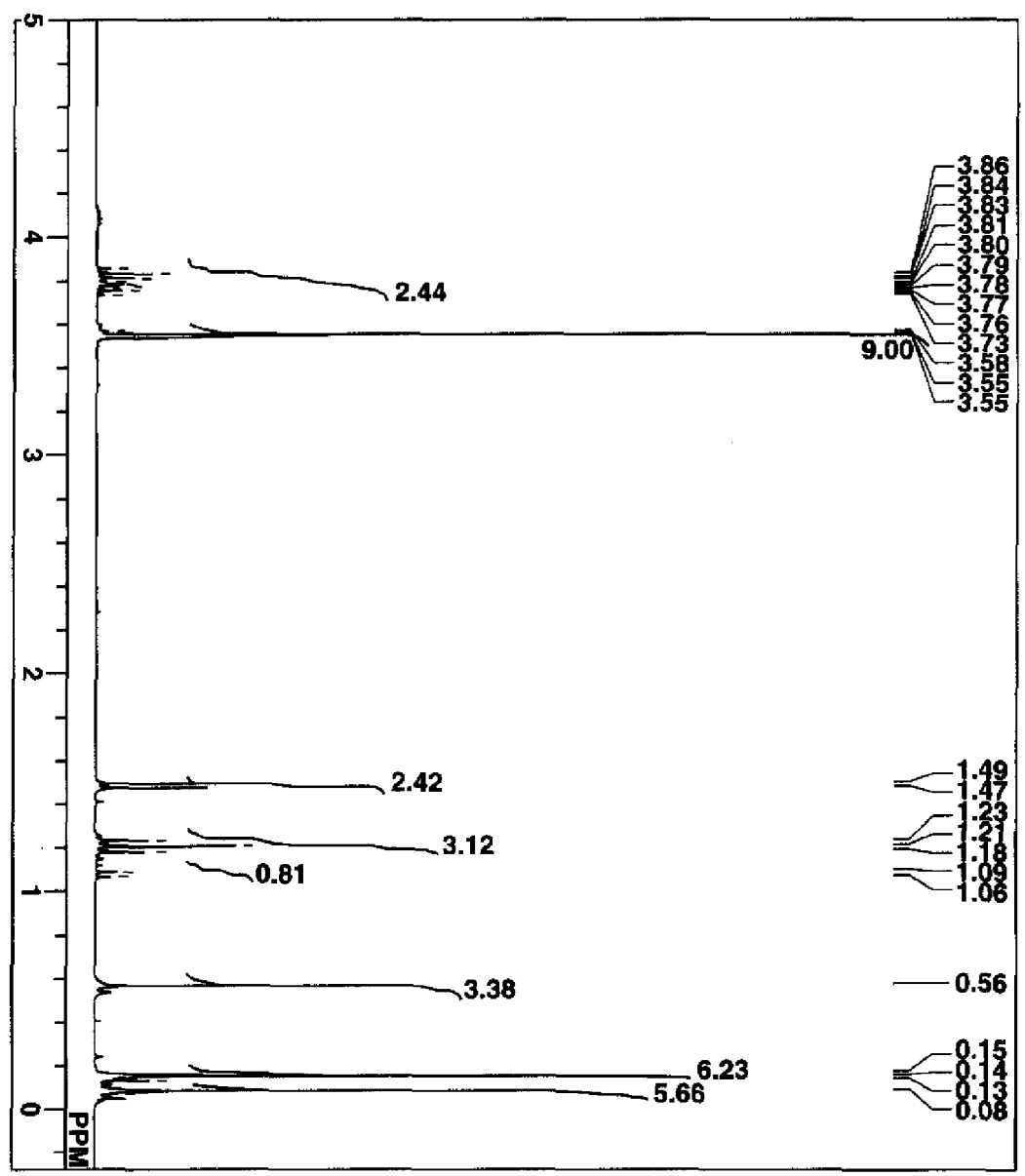
FIGS. 1, 2, 3, and 4 are $^1$H-NMR, $^{13}$C-NMR, $^{29}$Si-NMR, and IR diagrams of target product (1) obtained in Example 1, respectively.

The organosilicon compounds of the invention are silyl ketene acetal compounds having a partial structure of the formula (1), and more specifically, silyl ketene acetal compounds having the formula (2), both defined above.

In formula (1) and (2), R, $R^1$ and $R^2$ are each independently selected from monovalent hydrocarbon groups of 1 to 12 carbon atoms, which may be straight, branched or cyclic. Exemplary are straight alkyl groups such as methyl, ethyl, propyl, n-butyl, hexyl, heptyl, octyl, nonyl, and decyl; cyclic alkyl groups such as cyclohexyl; and branched alkyl groups such as t-butyl and 2-ethylhexyl. Also included are halosubstituted monovalent hydrocarbon groups in which some or all hydrogen atoms on the foregoing groups are substituted by halogen atoms such as chloro, fluoro and bromo, for example, chlolomethyl, bromoethyl and trifluoropropyl. The groups represented by R, $R^1$ and $R^2$ may be the same or different. It is preferred in the practice of the invention that R and $R^1$ be methyl or ethyl, and $R^2$ be methyl, ethyl, n-butyl or 2-ethylhexyl.

The subscript n is an integer of 1 to 6, and preferably 2 to 4, and "a" is an integer of 1 to 3.

The organosilicon compounds of formula (2) are efficiently reactive with alcohols and silanols by virtue of the silyl ketene acetal structure having a silicon-oxygen bond which cleaves under relatively mild conditions. Accordingly, these novel organosilicon compounds are useful as a terminal alkoxysilylating agent for organopolysiloxanes such as industrially valuable α,ω-dihydroxypolydimethylsiloxane, or as a surface treating agent for silica, and a scavenger for alcohols, i.e., a storage stabilizer in alcohol removal type RTV compositions. Where three methoxy groups are included in the molecule, the compounds are trifunctional alkoxysilanes which are also useful as a curing agent in alcohol removal type RTV compositions.

Preparation Process

The silyl ketene acetal compounds of the invention can be prepared by reacting acrylic esters with hydroalkoxysiloxanes. This reaction is depicted by the following scheme [1], for example.

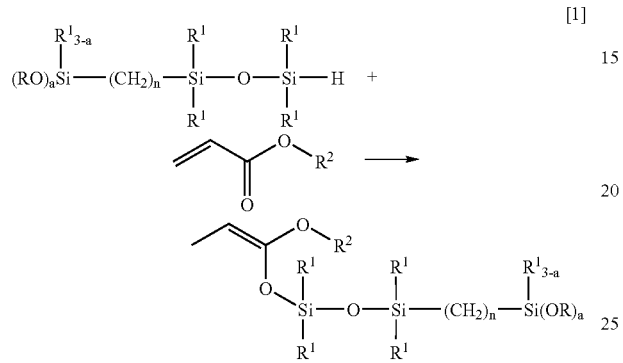

Note that R, $R^1$, $R^2$, n and "a" are as defined above. As understood from scheme [1] the reaction is a 1,4-addition reaction of a hydrosilyl (SiH) group on the siloxane compound to the acrylic ester.

Preferred examples of the hydrosiloxane compound which can be used herein are shown below.

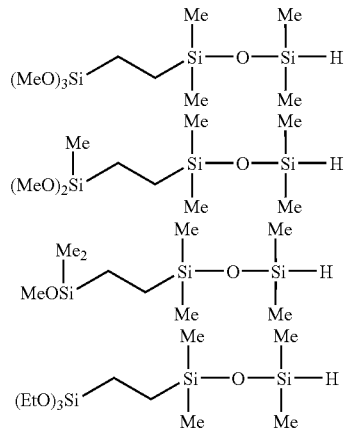

Note that Me stands for methyl and Et stands for ethyl.

Preferred examples of the acrylic ester which can be used for reaction with the hydrosiloxane compound include methyl acrylate, ethyl acrylate, n-butyl acrylate, and 2-ethylhexyl acrylate.

For the reaction, the hydrosiloxane compound and the acrylic ester are preferably used in such amounts that 0.8 to 1.2 moles of the acrylic ester is present per mole of the hydrosiloxane compound.

Most often, the reaction is carried out in the presence of an addition reaction catalyst. Suitable catalysts include platinum group metal catalysts, such as platinum, palladium and rhodium based catalysts, with the platinum based catalysts being preferred. Exemplary platinum based catalysts include platinum black, solid platinum on supports such as alumina and silica, chloroplatinic acid, alcohol-modified chloroplatinic acid, complexes of chloroplatinic acid with olefins, and platinum-vinyl siloxane complexes. The catalysts are used in catalytic amounts, for example, in amounts of 0.1 to 1000 ppm, and more preferably 0.5 to 100 ppm of platinum group metal based on the total weight of the acrylic ester and hydroalkoxysiloxane.

The reaction is generally carried out at a temperature of 50 to 120° C., desirably 60 to 100° C., for about 0.5 to 12 hours, desirably about 1 to 6 hours. The reaction will take place with no solvents. However, suitable solvents such as toluene and xylene may be used insofar as this does not adversely affect the addition reaction.

During the reaction according to scheme [1], isomers having the formulae (3) and (4) form in very minor amounts as side-reaction products in addition to the desired organosilicon compound.

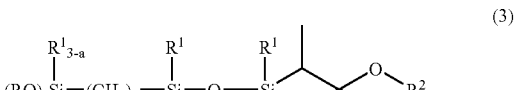

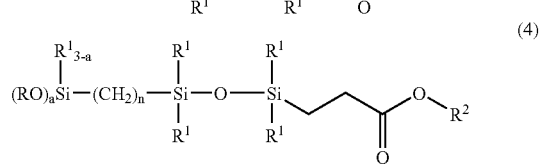

Note that R, $R^1$, $R^2$, n and "a" are as defined above.

These by-products are present in very small amounts and do not adversely affect the desired organosilicon compound because they are isomers of the desired organosilicon compound. Then, without separating the by-products, the reaction product may be used in a particular application as the terminal alkoxysilylating agent, surface treating agent, storage stabilizer, curing agent or the like.

EXAMPLE

Examples of the invention are given below by way of illustration and not by way of limitation. Me stands for methyl and Et stands for ethyl.

Example 1

A 500-ml four-necked flask equipped with a stirrer, reflux condenser, thermometer and dropping funnel was charged with 100.12 g (1 mole) of ethyl acrylate, 0.23 g of chloroplatinic acid ($H_2PtCl_6 \cdot 6H_2O$), 1.4 g of Irganox 1330 (polymerization inhibitor, Ciba Geigy), and 1.4 g of 2,6-di-t-butyl-4-methylphenol (polymerization inhibitor, Ciba Geigy). With stirring and heating, the temperature was raised to 70° C.

With stirring, 282.5 g (1 mole) of hydrosiloxane compound #1, shown below, was added dropwise to the flask, during which an exotherm was noted and the temperature became 70 to 80° C. The reaction system was held at the temperature for 4 hours. At the end of reaction, vacuum distillation gave 314 g (yield 82%) of a fraction having a boiling point of 130-132° C./7 mmHg.

Figure 2:
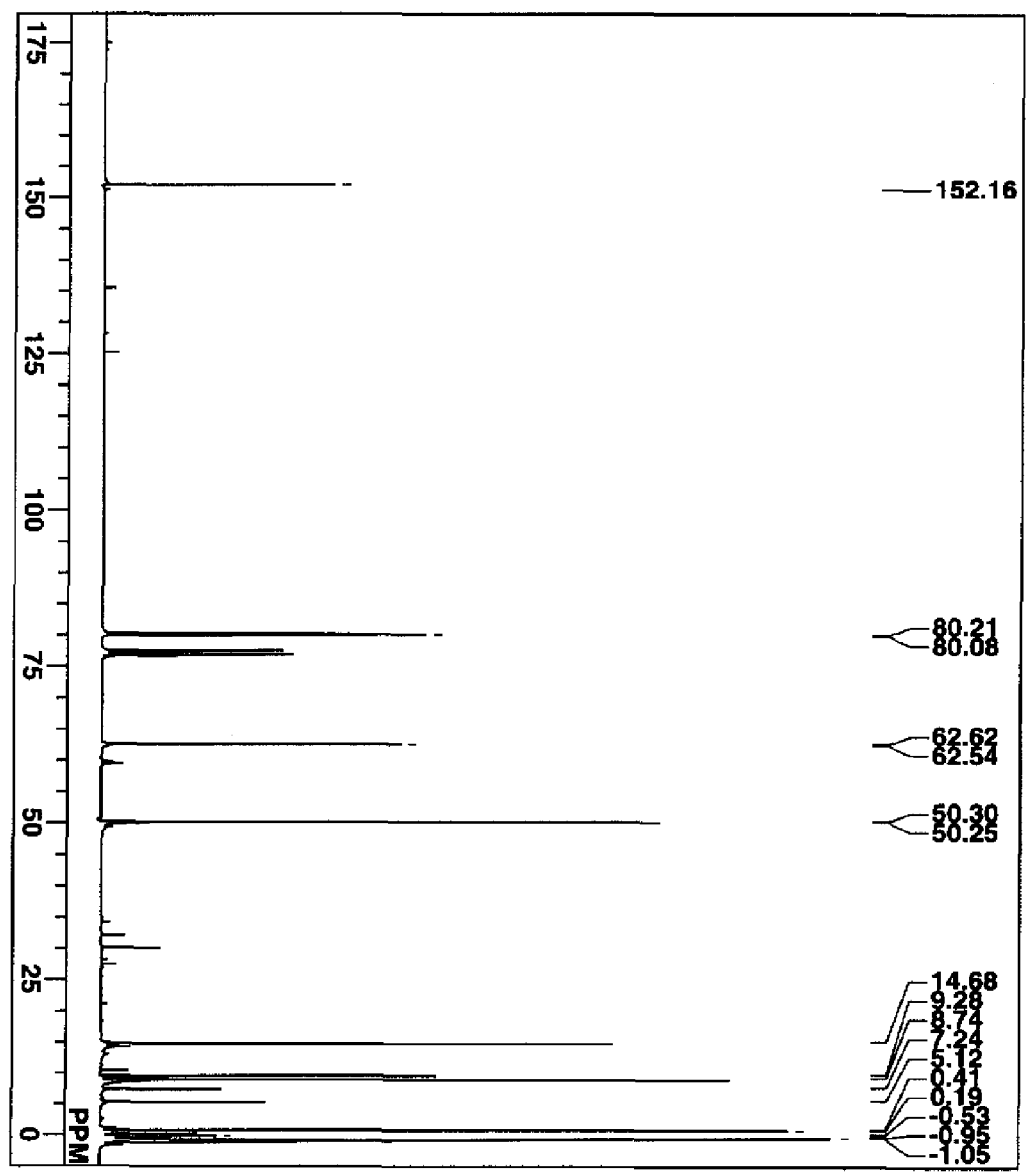
Figure 3:
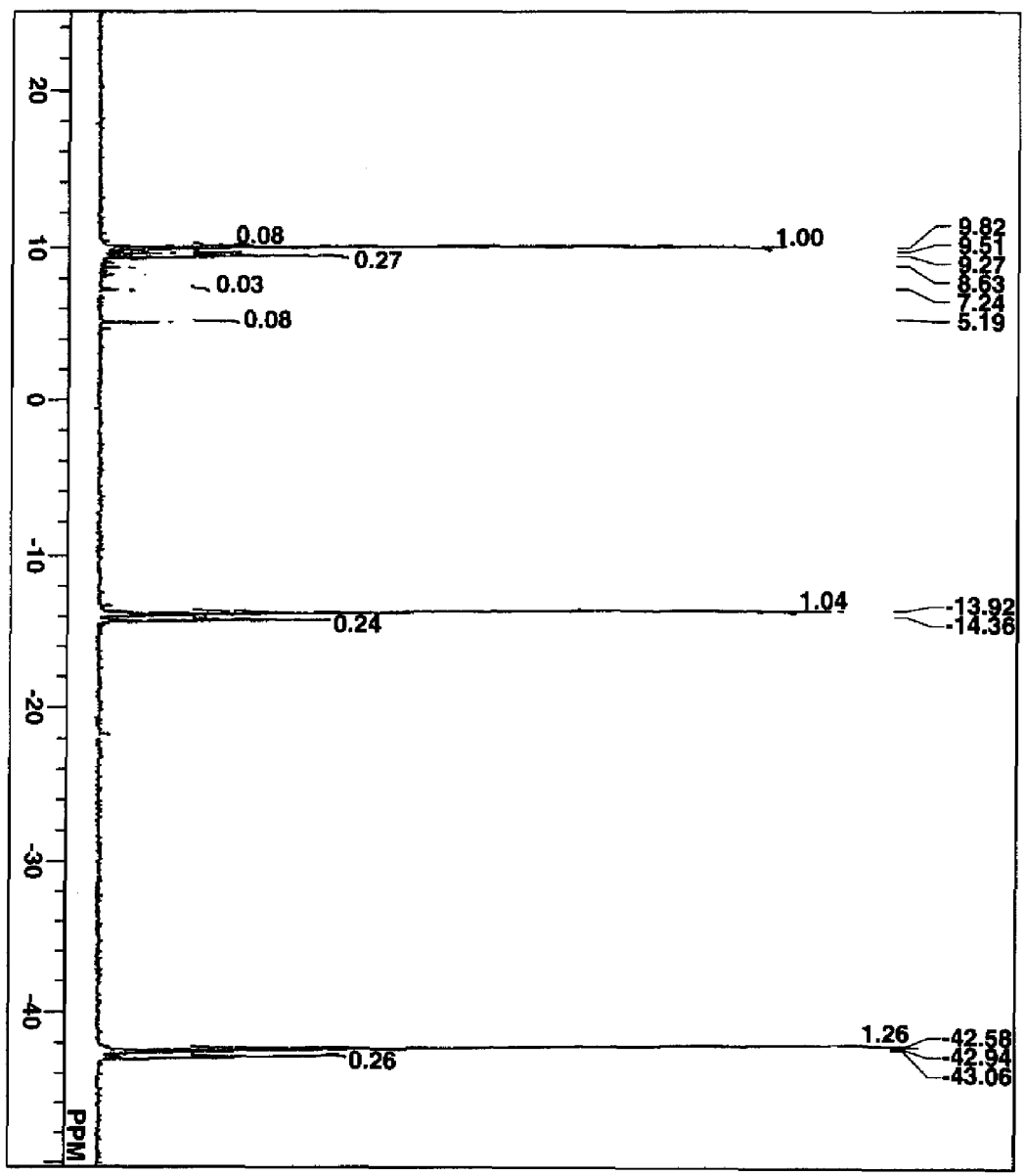
Figure 4:
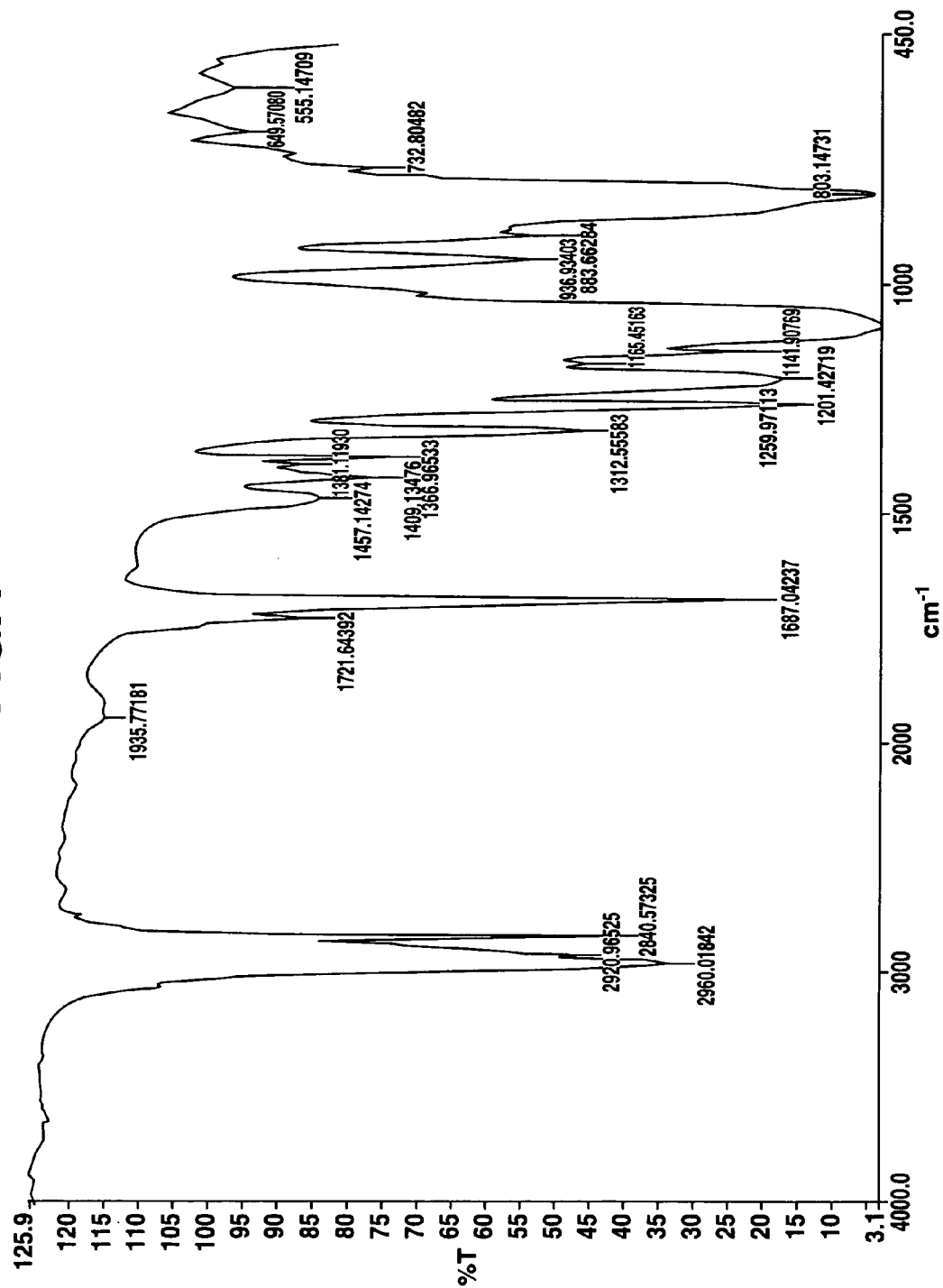
Figure 5:
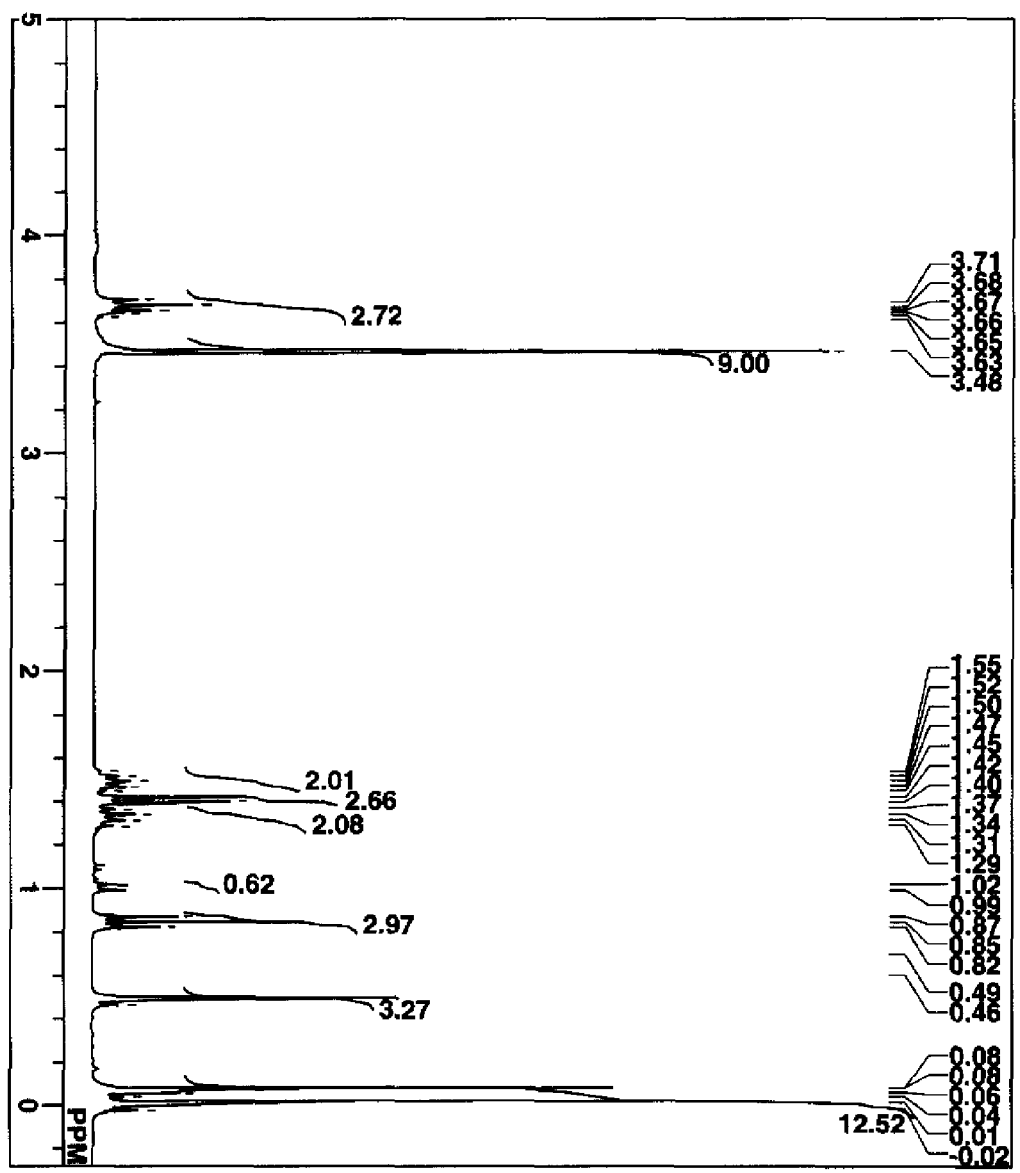
FIGS. 5, 6, 7, and 8 are $^1$H-NMR, $^{13}$C-NMR, $^{29}$Si-NMR, and IR diagrams of target product (2) obtained in Example 2, respectively.
Figure 6:
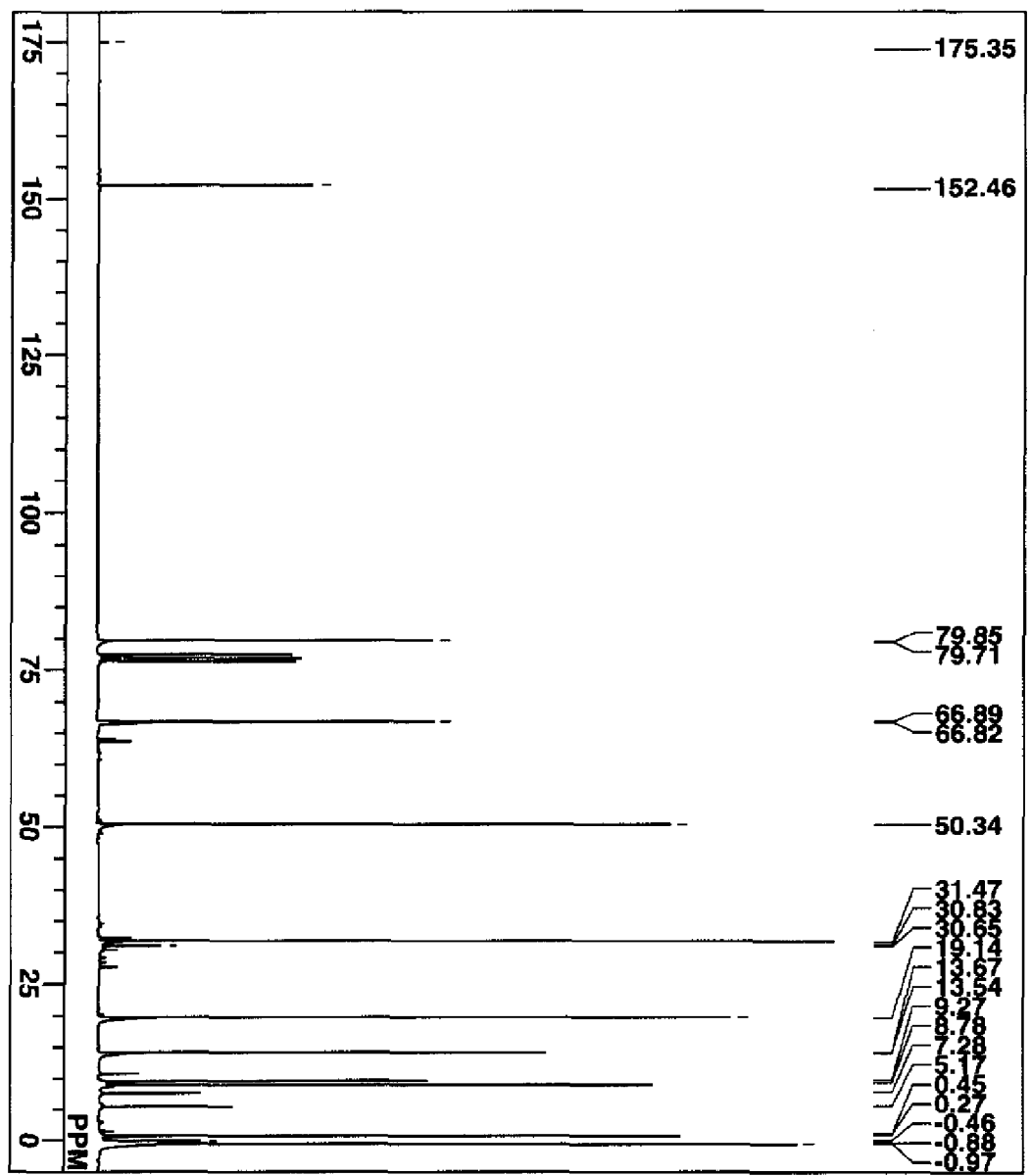
Figure 7:
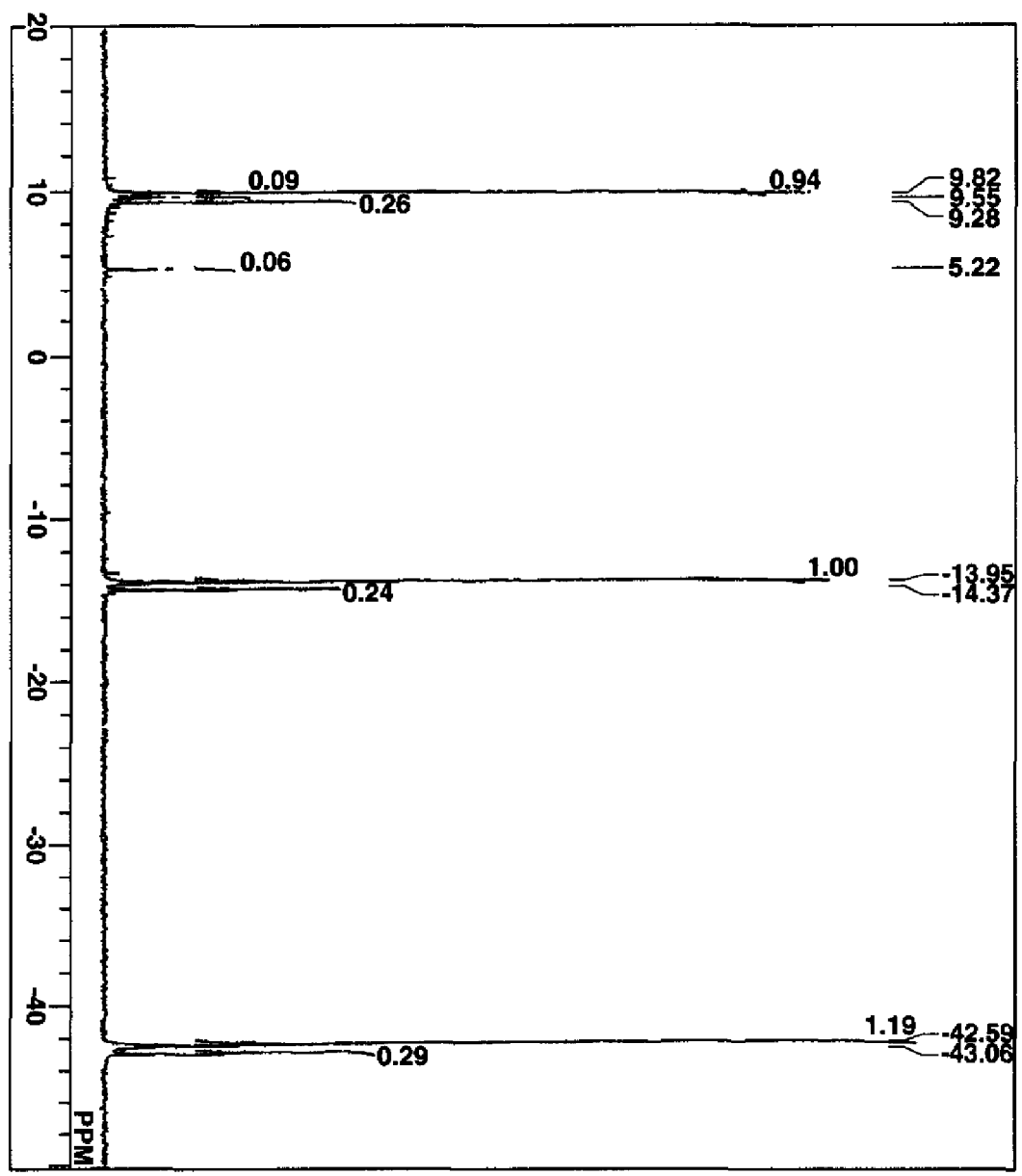
Figure 8:
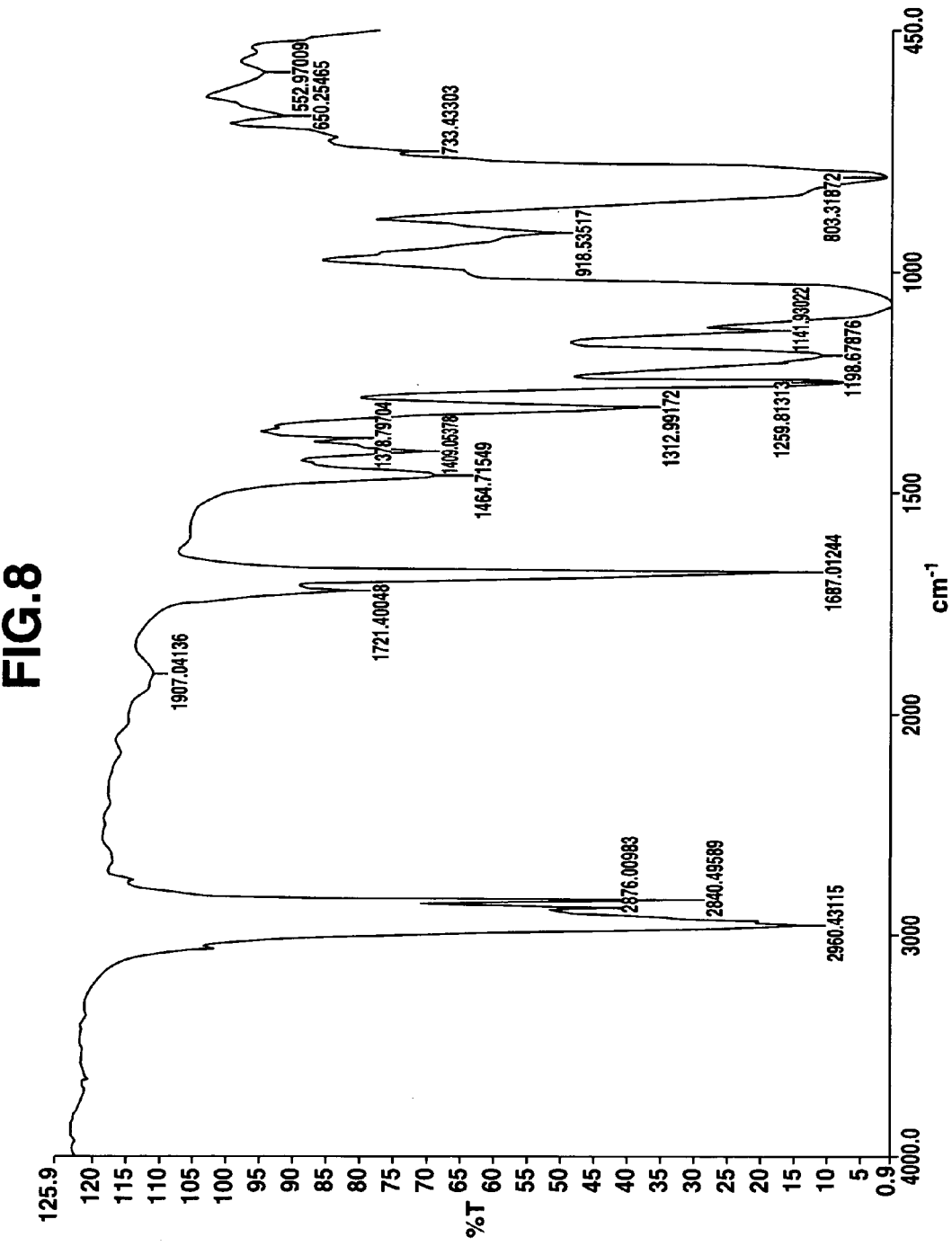
Figure 9:
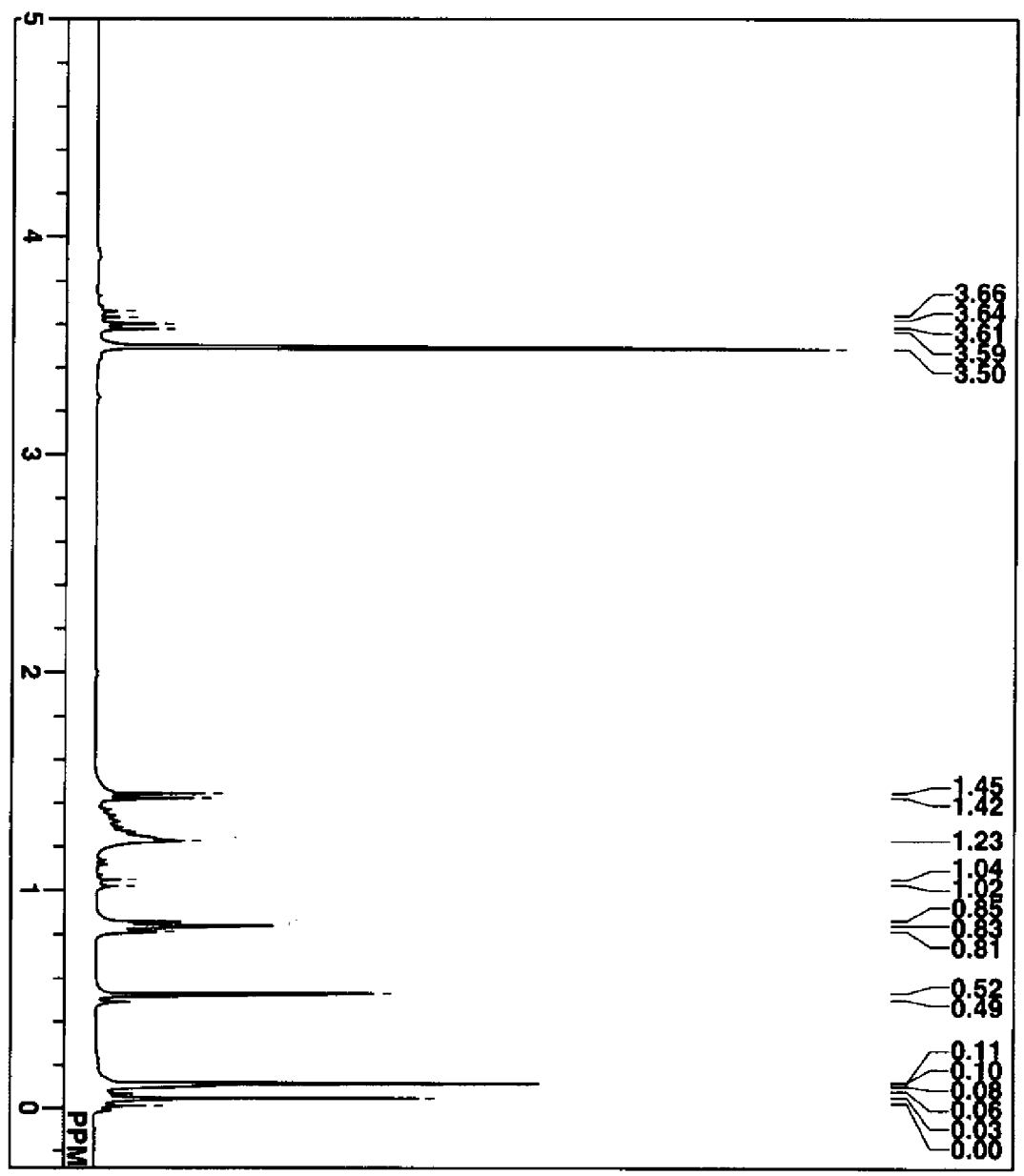
FIGS. 9, 10, 11, and 12 are $^1$H-NMR, $^{13}$C-NMR, $^{29}$Si-NMR, and IR diagrams of target product (3) obtained in Example 3, respectively.
Figure 10:
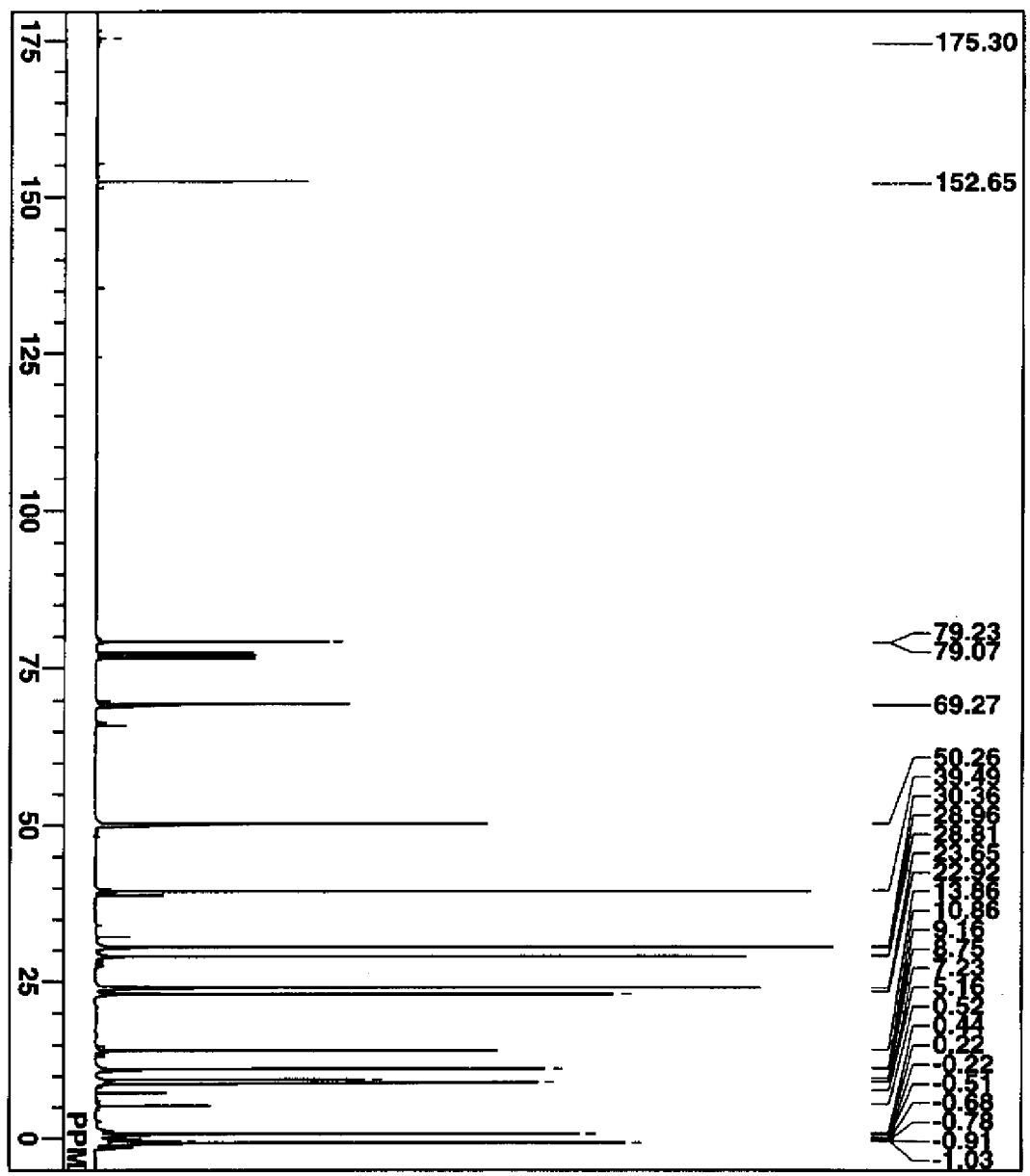
Figure 11:
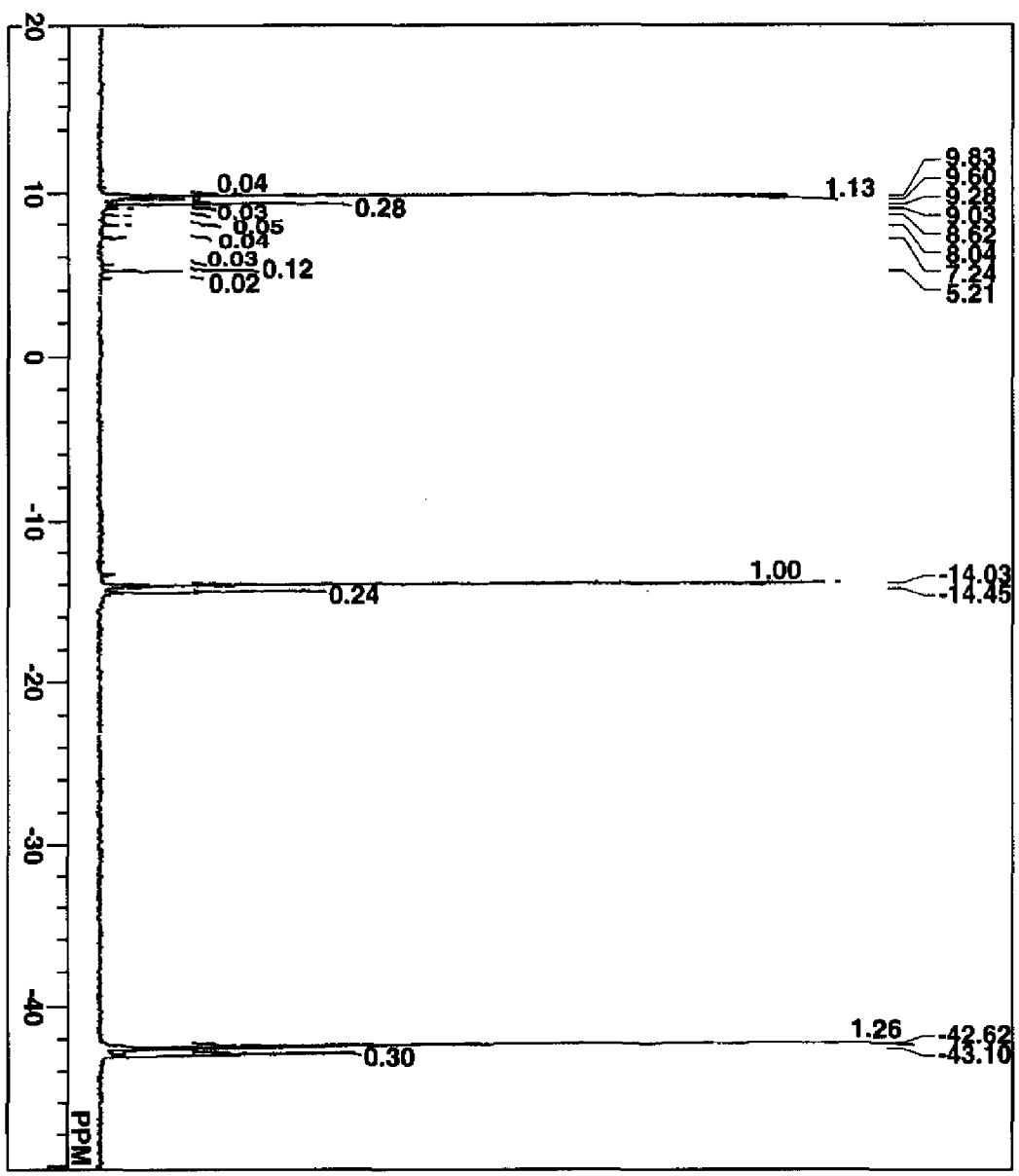
Figure 12:
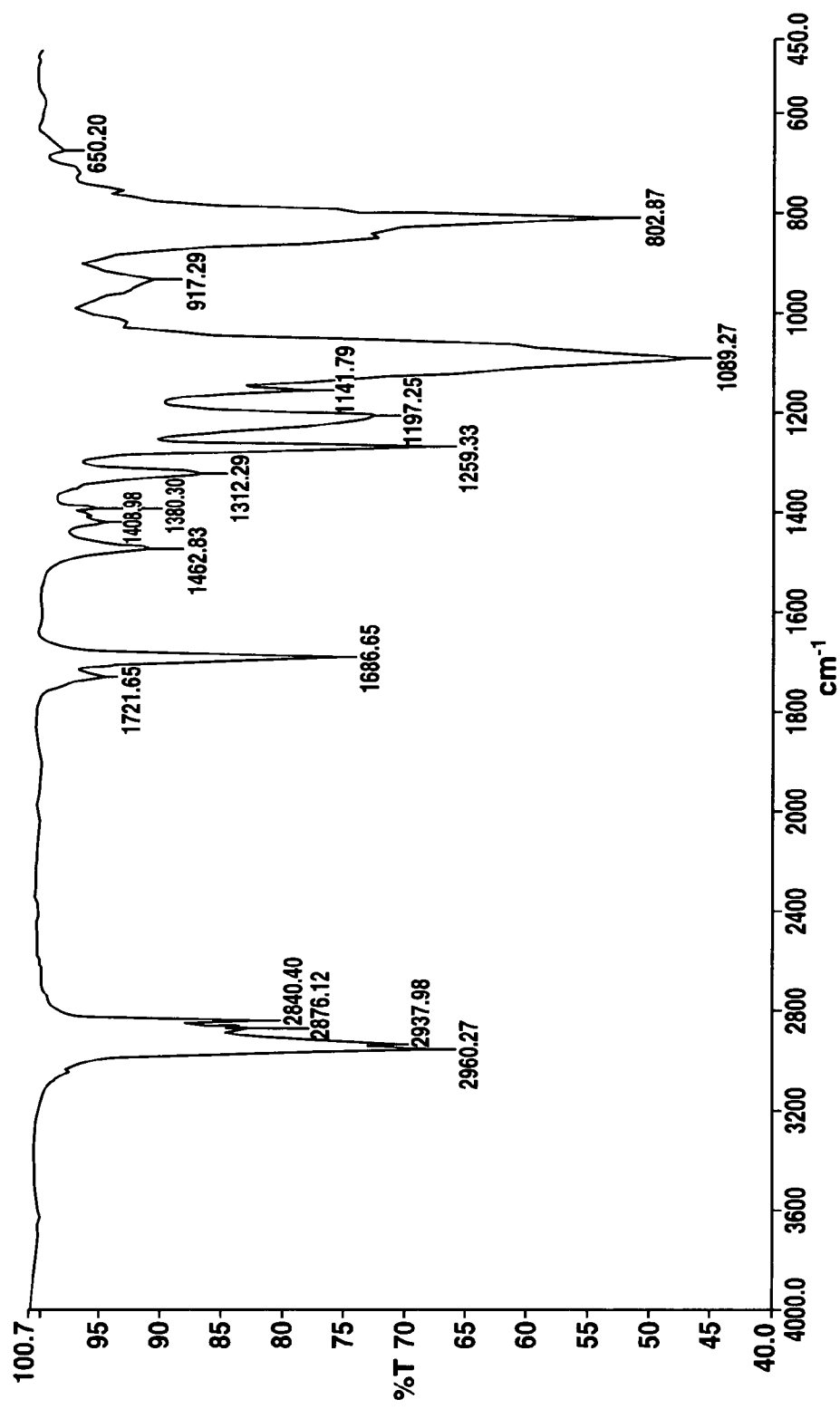
Figure 13:
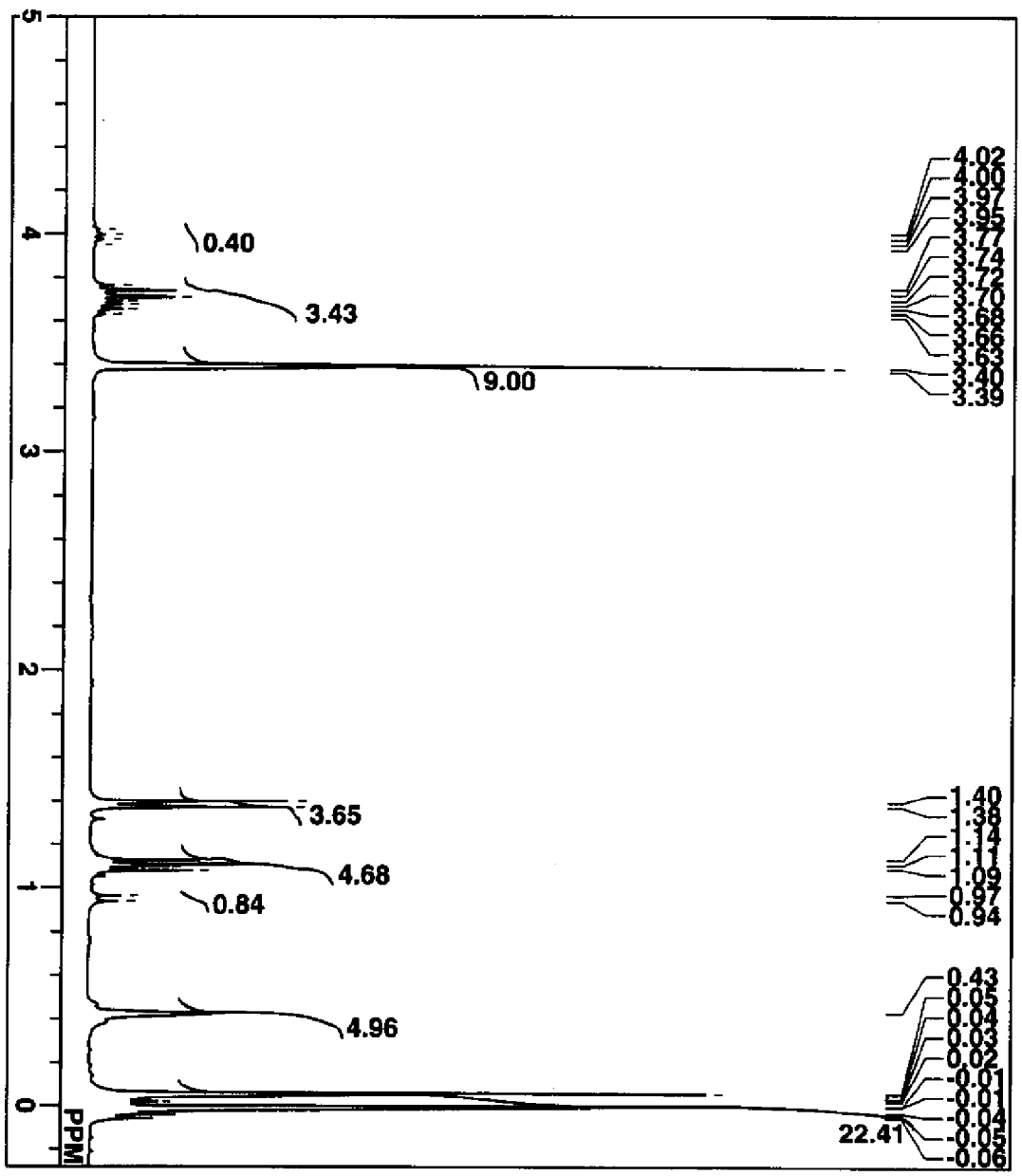
FIGS. 13, 14, 15, and 16 are $^1$H-NMR, $^{13}$C-NMR, $^{29}$Si-NMR, and IR diagrams of target product (4) obtained in Example 4, respectively.
Figure 14:
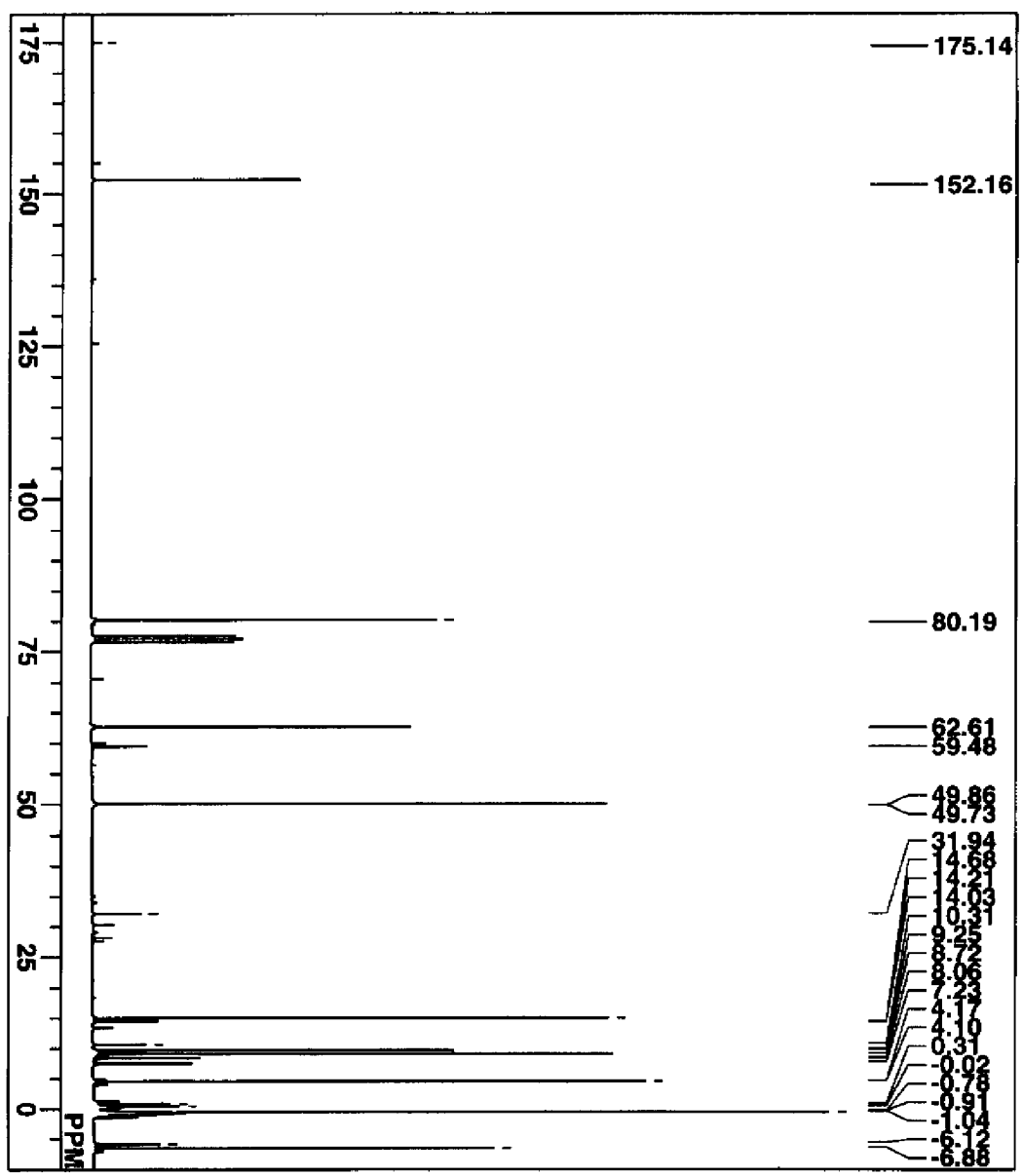
Figure 15:
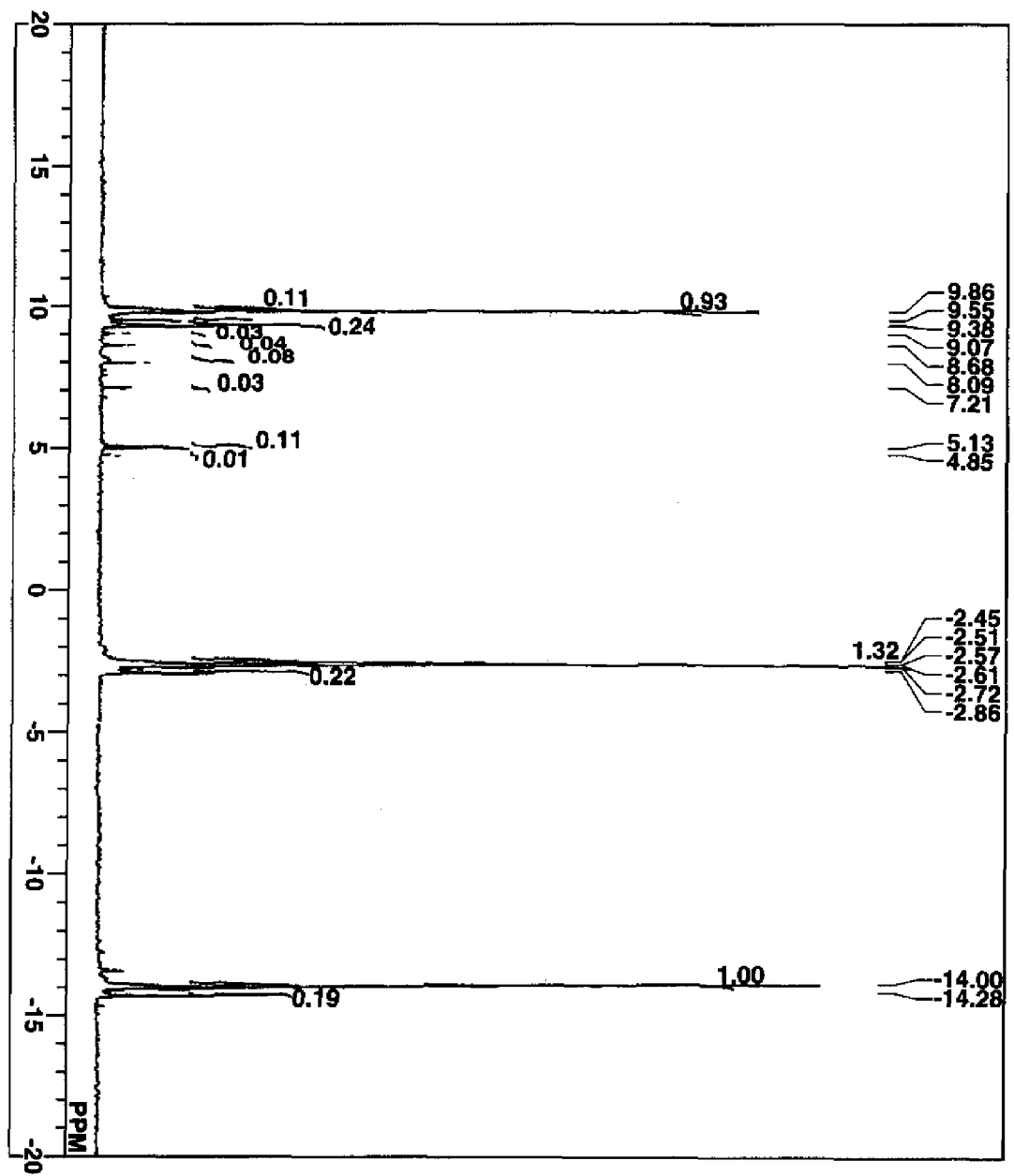
Figure 16:
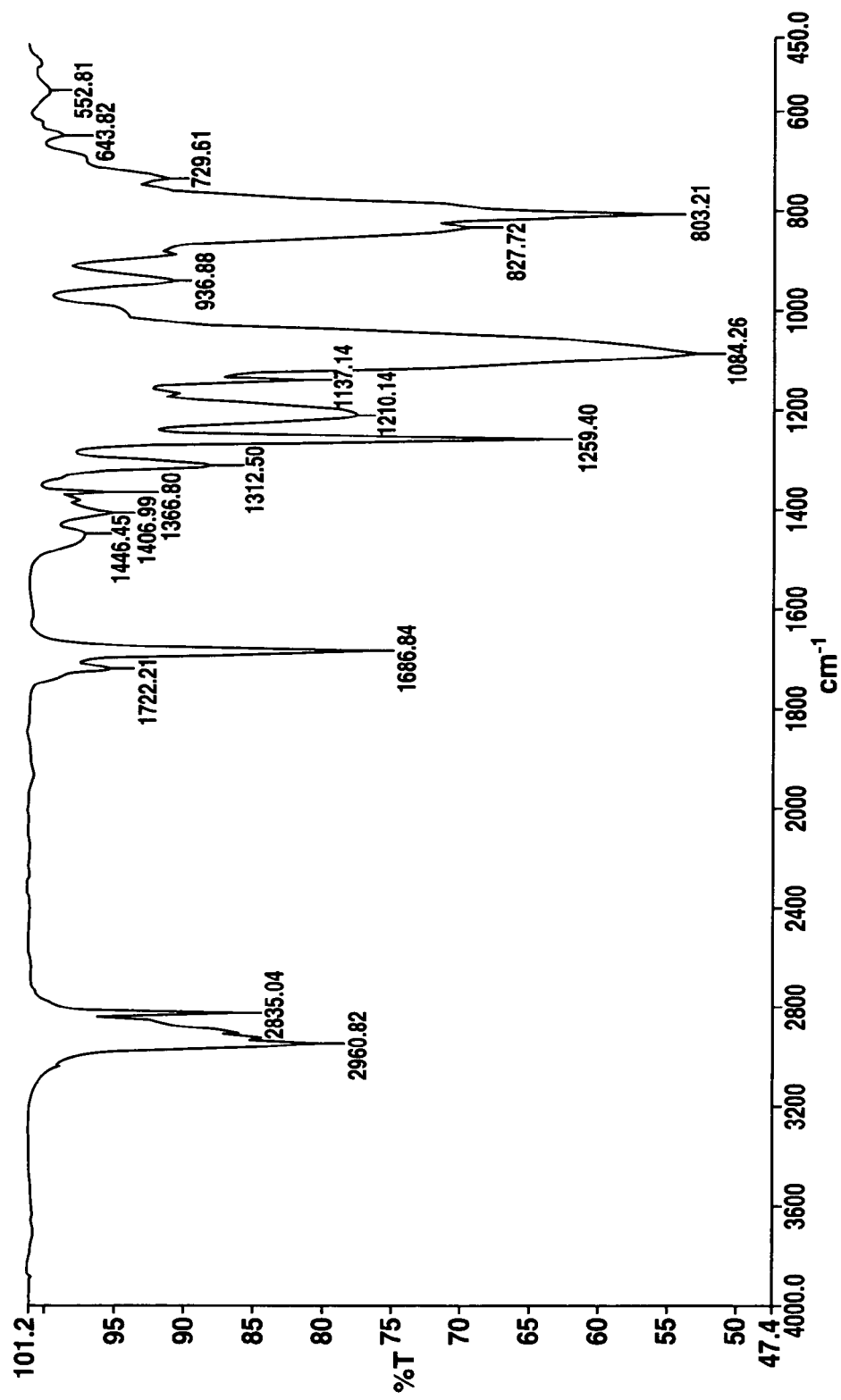
Figure 17:
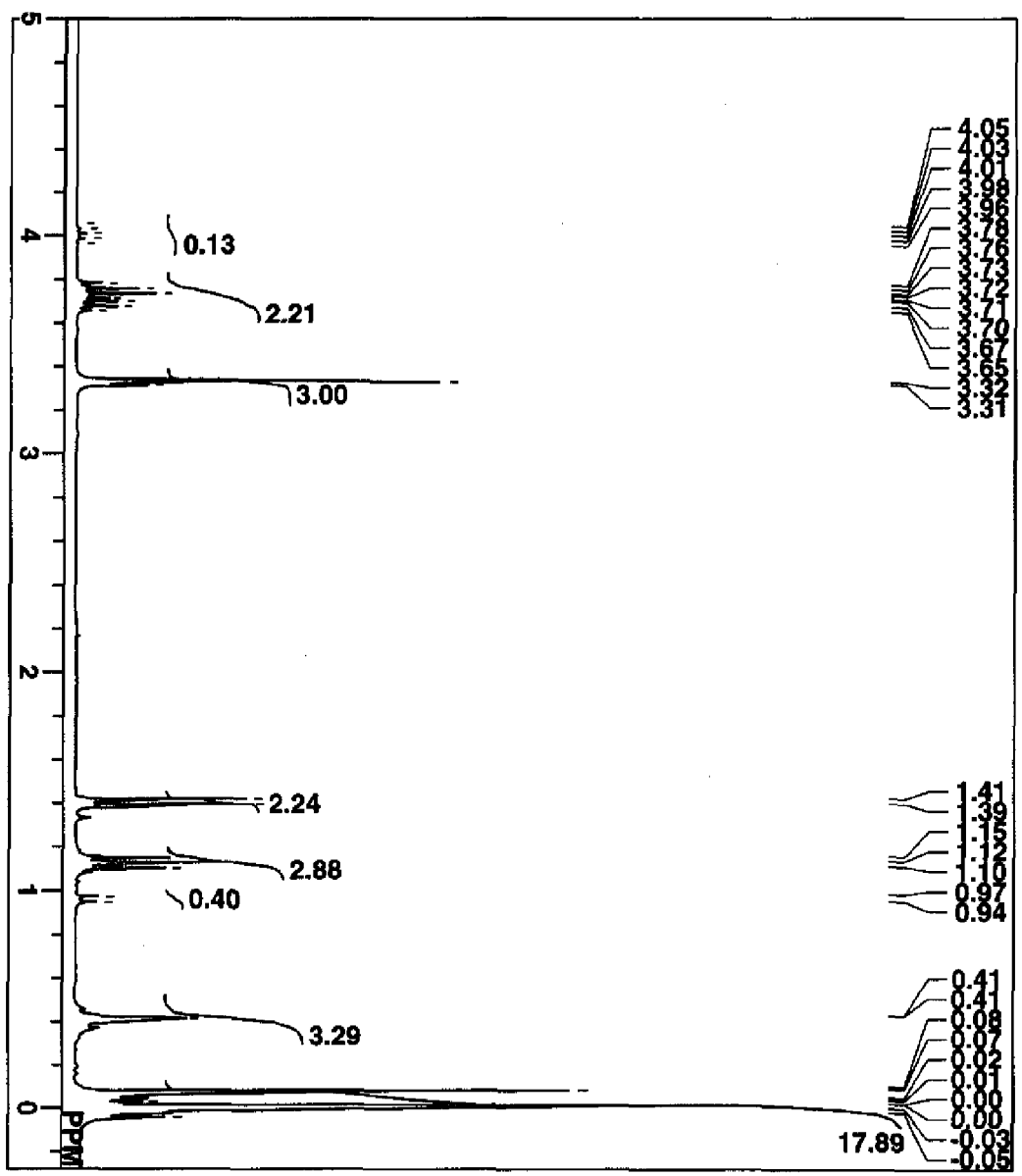
FIGS. 17, 18, 19, and 20 are $^1$H-NMR, $^{13}$C-NMR, $^{29}$Si-NMR, and IR diagrams of target product (5) obtained in Example 5, respectively.
Figure 18:
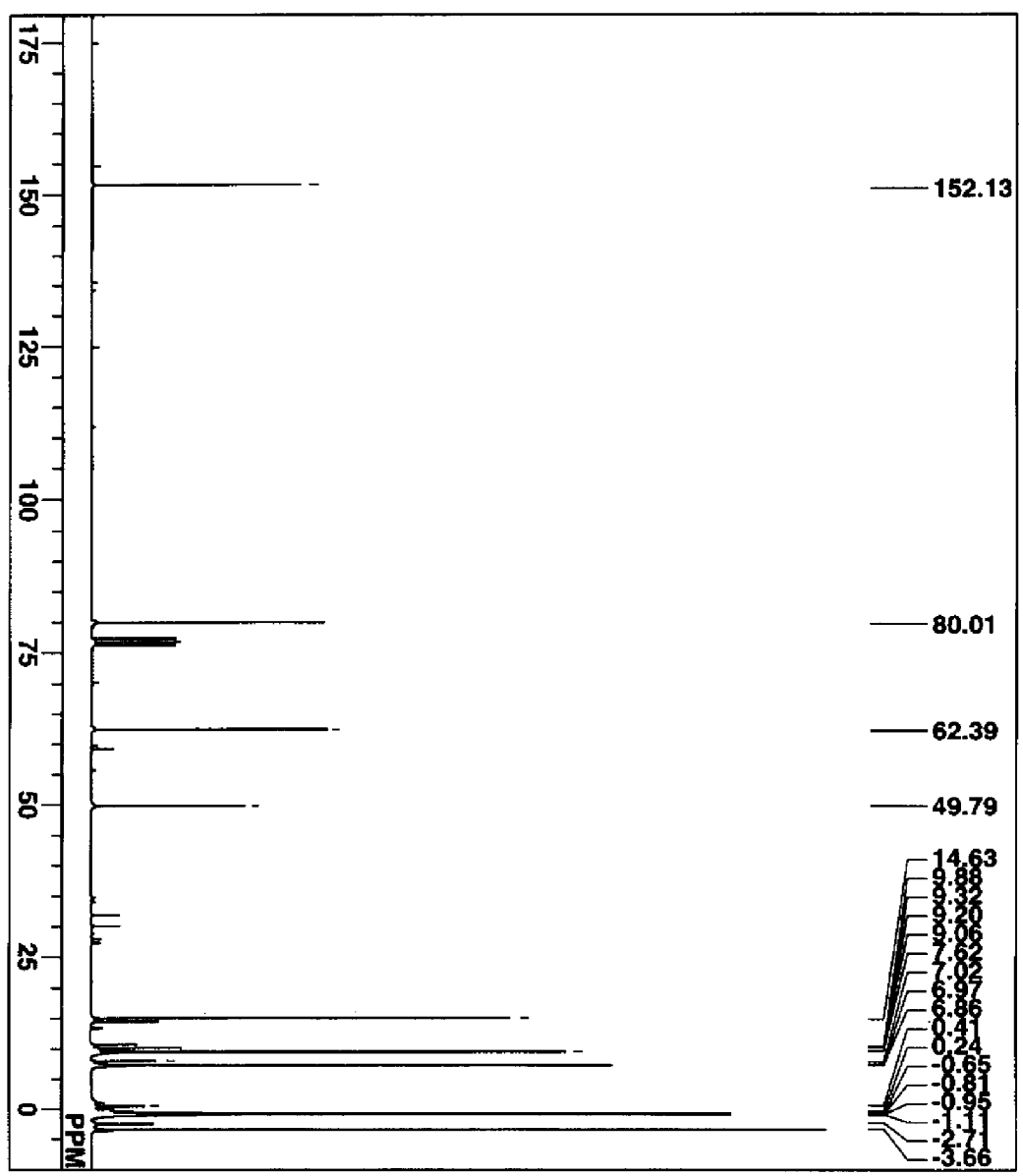
Figure 19:
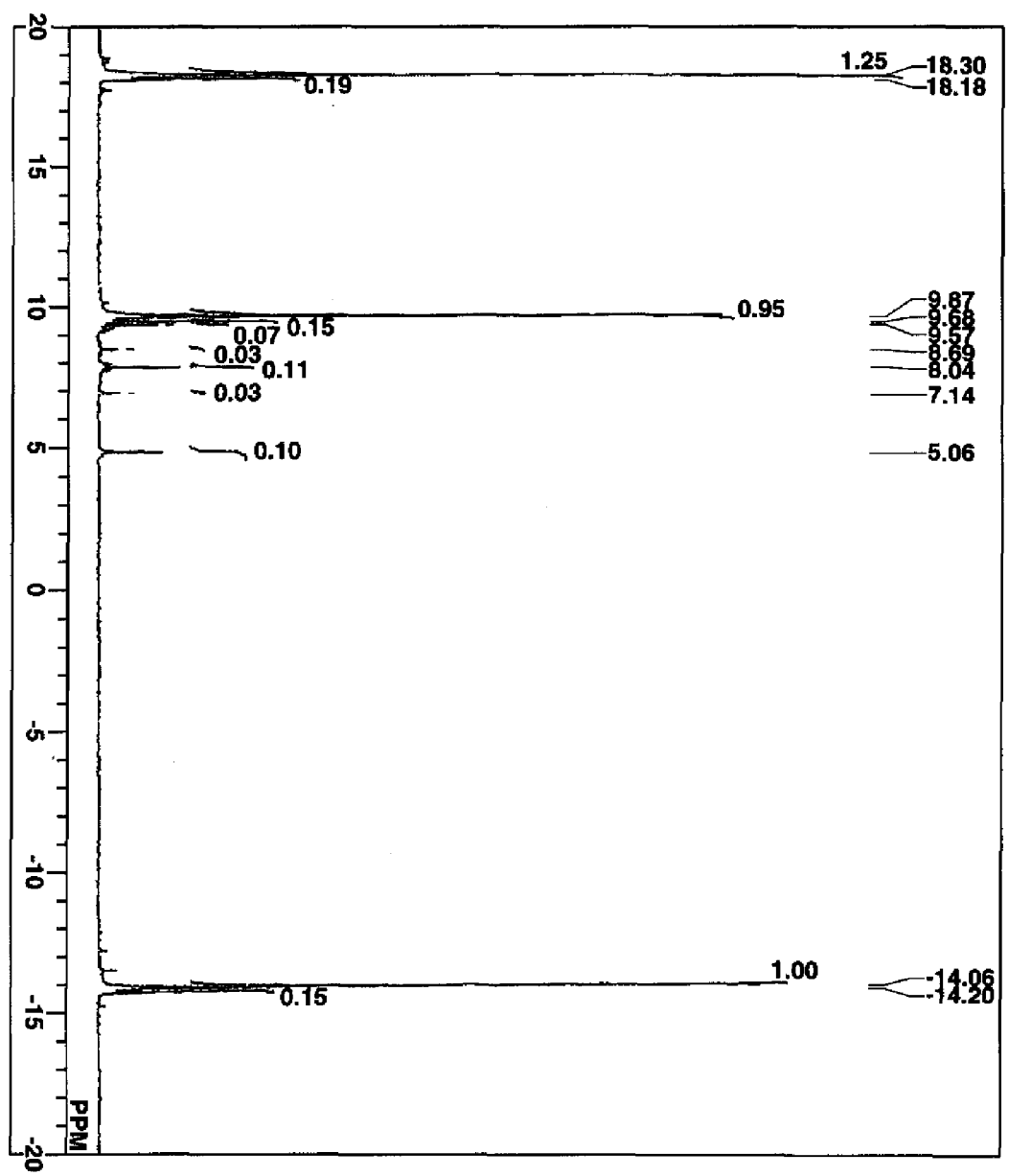
Figure 20:
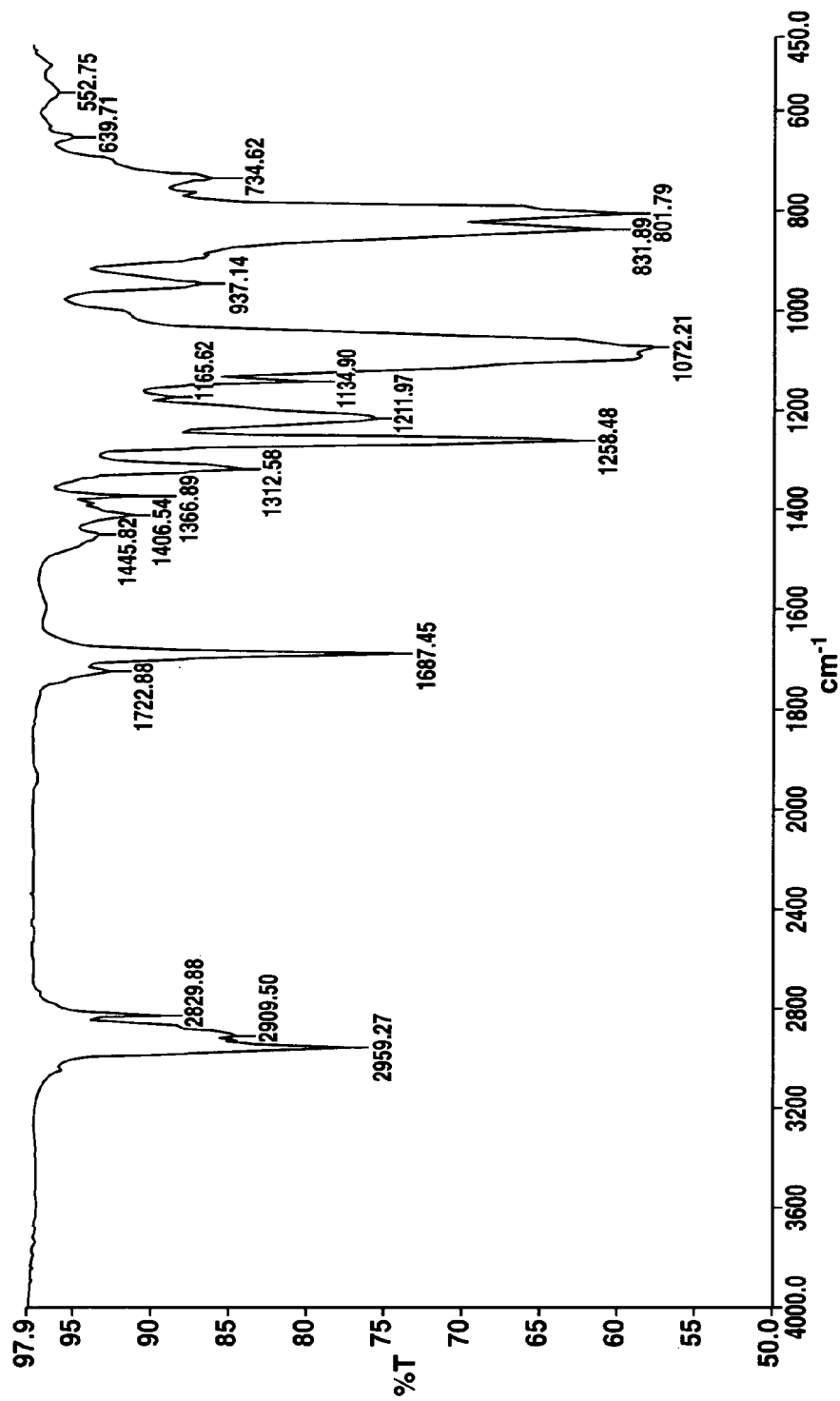

On gas chromatography (GC) analysis, the fraction was found to contain at least 97% of the target product (1). The product was analyzed by $^1$H-NMR, $^{13}$C-NMR, and $^{29}$Si-NMR spectroscopy, with the diagrams shown in FIGS. 1, 2, and 3, respectively. An IR analysis diagram of the product is shown in FIG. 4.

Hydrosiloxane Compound #1

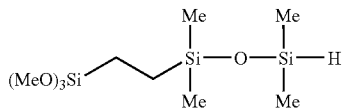

Target Product (1)

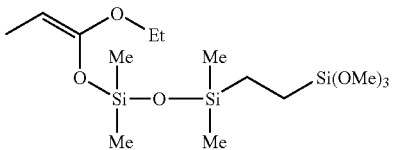

Examples 2 to 5

Synthesis was carried out as in Example 1, using the acrylic ester and hydrosiloxane compound shown in Table 1. The data of GC analysis of products (2) to (5) are shown in Table 1. The $^1$H-NMR, $^{13}$C-NMR, $^{29}$Si-NMR, and IR diagrams of these products are shown in FIGS. 5 to 20.

TABLE 1

|  | Example | | | | |
| --- | --- | --- | --- | --- | --- |
|  | 1 | 2 | 3 | 4 | 5 |
| Ethyl acrylate (g) | 100.12 |  |  | 100.12 | 100.12 |
| n-Butyl acrylate (g) |  | 128.17 |  |  |  |
| 2-Ethymexyl acrylate (g) |  |  | 184.28 |  |  |
| Hydrosiloxane compound #1 (g) | 282.5 | 282.5 | 282.5 |  |  |
| Hydrosiloxane compound #2 (g) |  |  |  | 266.5 |  |
| Hydrosiloxane compound #3 (g) |  |  |  |  | 250.5 |
| Boiling point (° C./mmHg) | 130-132/5 | 149-152/5 | —*$^1$ | 120-123/7 | 115-120/8 |
| Purity *$^2$ (%) | 97 | 99 | 98 | 95 | 93 |
| Yield (%) | 85 | 81 | 80 | 82 | 86 |
| Target product | (1) | (2) | (3) | (4) | (5) |

*$^1$ distillation impossible, a product having a lower boiling point than the target product was removed by concentration under vacuum
*$^2$ purity of target product by GC analysis, impurities are side-reaction products Hydrosiloxane Compound #2

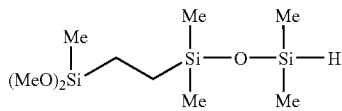

Hydrosiloxane Compound #3

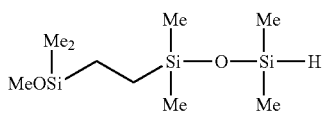

Target Product (2)

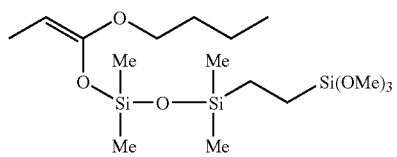

Target Product (3)

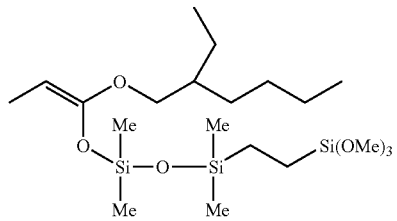

Target Product (4)

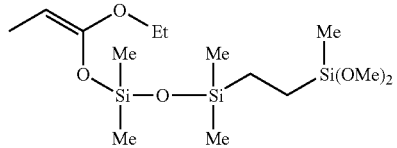

Target Product (5)

Japanese Patent Application No. 2006-306596 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:
1. A silyl ketene acetal compound having a partial structure of the formula (1):

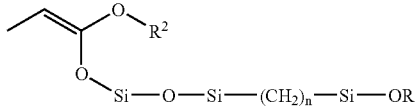

wherein R and $R^2$ are each independently a substituted or unsubstituted, monovalent hydrocarbon group of 1 to 12 carbon atoms, and n is an integer of 1 to 6.

2. The silyl ketene acetal compound of claim 1 having the formula (2):

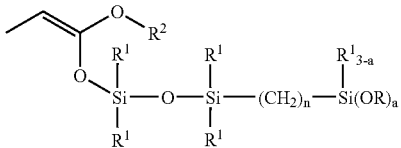

wherein R, $R^1$ and $R^2$ are each independently a substituted or unsubstituted, monovalent hydrocarbon group of 1 to 12 carbon atoms, n is an integer of 1 to 6, and "a" is an integer of 1 to 3.

* * * * *